US 12,350,452 B2

(12) United States Patent
Yamamoto et al.

(10) Patent No.: US 12,350,452 B2
(45) Date of Patent: Jul. 8, 2025

(54) CATHETER ASSEMBLY AND CATHETER INDWELLING BODY

(71) Applicant: TERUMO KABUSHIKI KAISHA, Tokyo (JP)

(72) Inventors: Shota Yamamoto, Mitaka (JP); Shinnosuke Yamashita, Ljubljana (SI)

(73) Assignee: TERUMO KABUSHIKI KAISHA, Tokyo (JP)

( * ) Notice: Subject to any disclaimer, the term of this patent is extended or adjusted under 35 U.S.C. 154(b) by 1025 days.

(21) Appl. No.: 17/338,495

(22) Filed: Jun. 3, 2021

(65) Prior Publication Data

US 2021/0283376 A1    Sep. 16, 2021

Related U.S. Application Data

(63) Continuation of application No. PCT/JP2019/046933, filed on Dec. 2, 2019.

(30) Foreign Application Priority Data

Dec. 4, 2018  (JP) ................................. 2018-227286

(51) Int. Cl.
*A61M 25/06* (2006.01)
*A61M 25/00* (2006.01)
*A61M 39/06* (2006.01)

(52) U.S. Cl.
CPC .... *A61M 25/0606* (2013.01); *A61M 25/0017* (2013.01); *A61M 25/007* (2013.01); *A61M 25/0097* (2013.01); *A61M 39/06* (2013.01)

(58) Field of Classification Search
CPC .......... A61M 25/0606; A61M 25/0017; A61M 25/007; A61M 25/0097; A61M 39/06
See application file for complete search history.

(56) References Cited

U.S. PATENT DOCUMENTS

2010/0204648 A1   8/2010   Stout et al.
2011/0160662 A1   6/2011   Stout et al.
(Continued)

FOREIGN PATENT DOCUMENTS

CN   103492012 A   1/2014
EP   3 932 460 A1  1/2022
(Continued)

OTHER PUBLICATIONS

Written Opinion of the International Search Authority, dated Feb. 18, 2020, issued in corresponding International Application No. PCT/JP2019/046933 (11 pages).
(Continued)

*Primary Examiner* — Phillip A Gray
(74) *Attorney, Agent, or Firm* — Foley & Lardner LLP

(57) ABSTRACT

A catheter assembly includes: an inner needle having a blade surface at a distal end; a catheter through which the inner needle is inserted; a catheter hub through which the inner needle is inserted and that is fixed to a proximal end of the catheter; a valve that comprises a pair of inclined portions that are inclined so as to become closer to each other in a distal direction, an end surface located at distal ends of the pair of inclined portions, and a slit formed along a longitudinal direction of the end surface, wherein the valve is located in an internal space of the catheter hub; and an opening member that is located in the internal space, is formed in a tubular shape, has a space inside, is located proximal of the valve in an initial state, and is configured to move in a distal direction to open the valve.

18 Claims, 13 Drawing Sheets

(56) References Cited

U.S. PATENT DOCUMENTS

| | | | |
|---|---|---|---|
| 2012/0197201 | A1 | 8/2012 | Tanabe et al. |
| 2013/0090607 | A1* | 4/2013 | McKinnon ........ A61M 39/0693 |
| | | | 604/247 |
| 2013/0204226 | A1 | 8/2013 | Keyser |
| 2020/0376235 | A1 | 12/2020 | Shevgoor et al. |

FOREIGN PATENT DOCUMENTS

| | | | |
|---|---|---|---|
| JP | 2002-263197 | A | 9/2002 |
| JP | 2012-517326 | A | 8/2012 |
| JP | 2013-535997 | A | 9/2013 |
| JP | 2014-528330 | A | 10/2014 |
| JP | 2015-511149 | A | 4/2015 |
| JP | 2017-514575 | A | 6/2017 |
| JP | 2018-511439 | A | 4/2018 |
| WO | WO-2018/181196 | A1 | 10/2018 |

OTHER PUBLICATIONS

Extended European Search Report in EP Appl. Ser. No. 19892085.2 dated May 17, 2022 (17 pages).
International Searching Authority, "International Search Report," issued in connection with International Patent Application No. PCT/JP2019/046933, dated Feb. 18, 2020.
International Searching Authority, "Written Opinion," issued in connection with International Patent Application No. PCT/JP2019/046933, dated Feb. 18, 2020.
First Chinese Office Action issued in connection with CN Appl. Ser. No. 201980074068.5 dated Jul. 22, 2022.

* cited by examiner

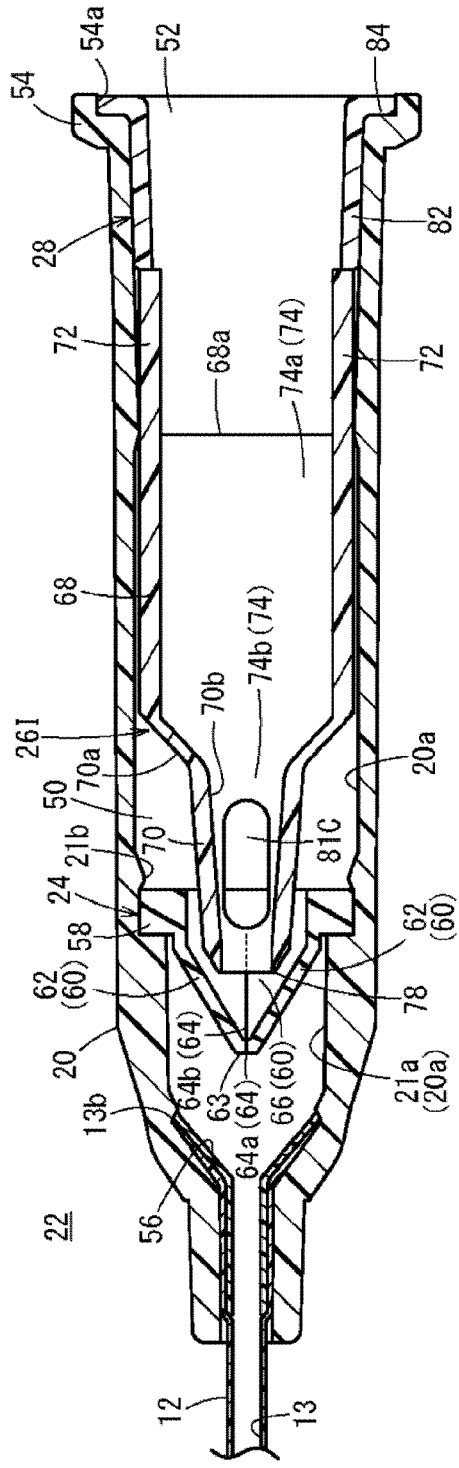
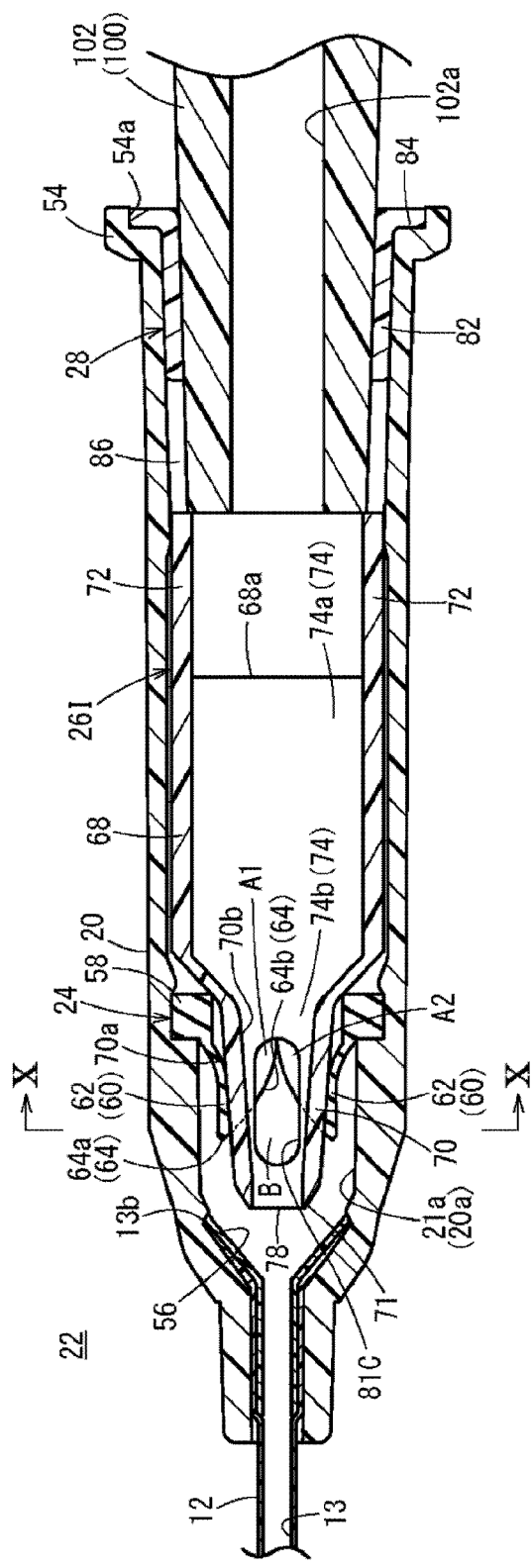
FIG. 9A
FIG. 9B

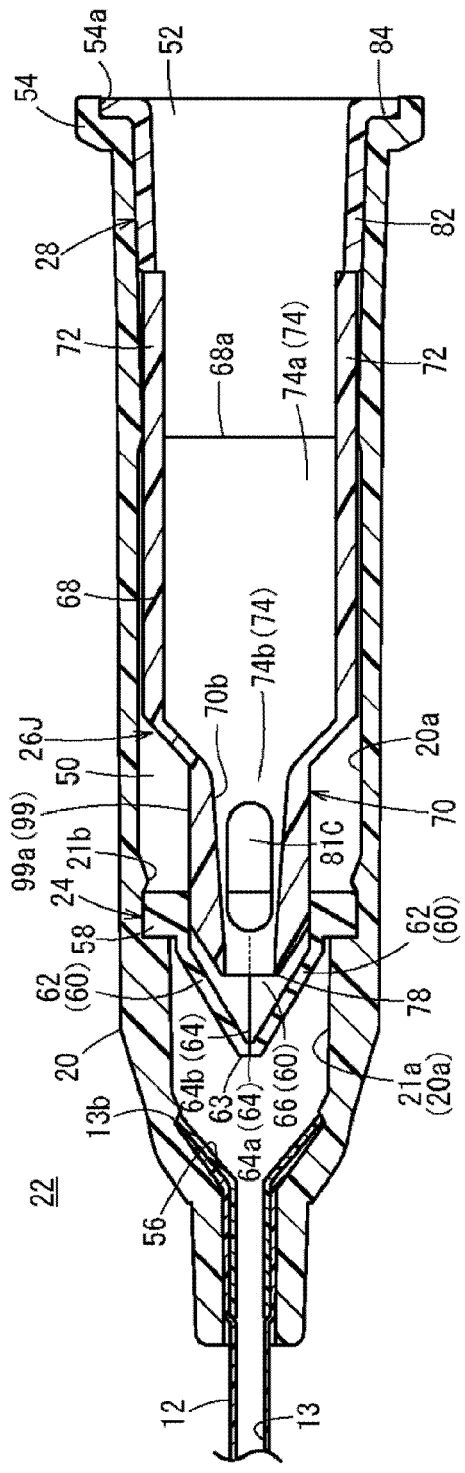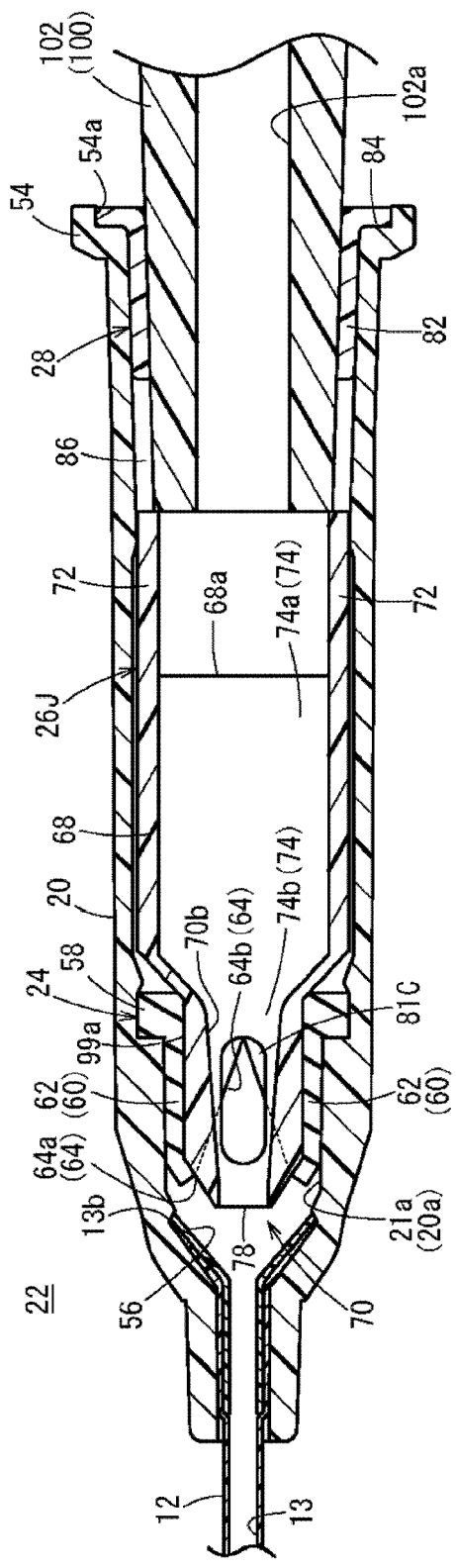

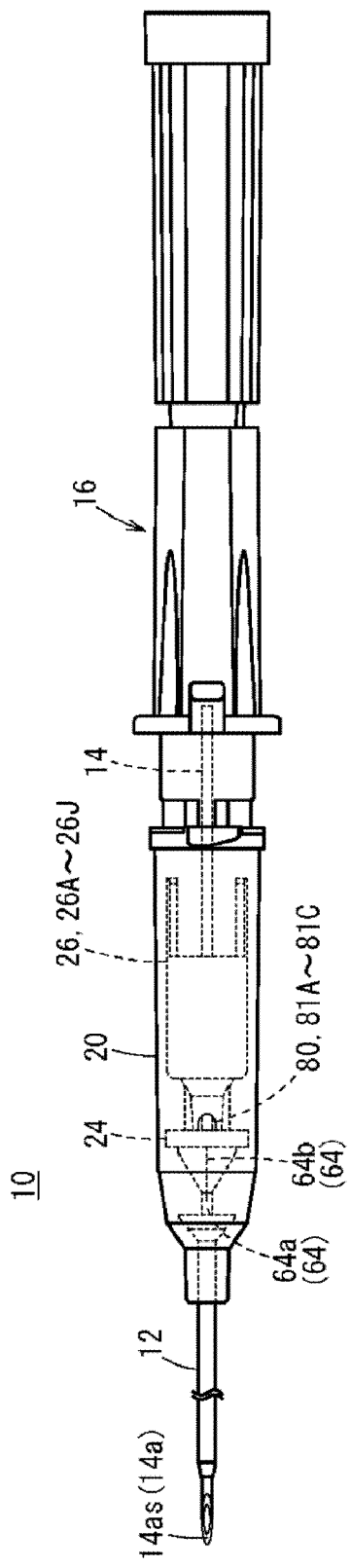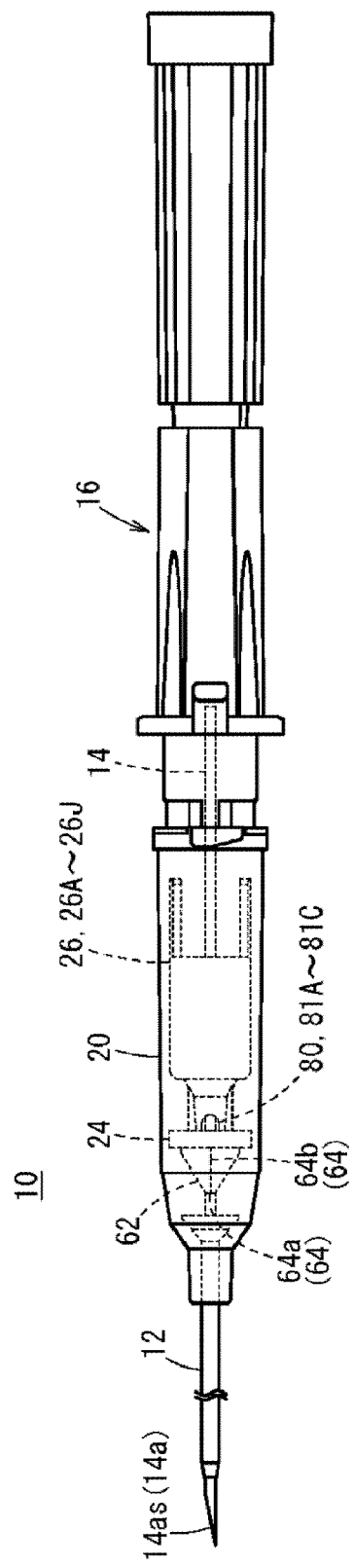

CATHETER ASSEMBLY AND CATHETER INDWELLING BODY

CROSS-REFERENCE TO RELATED APPLICATIONS

This application is a bypass continuation of PCT Application No. PCT/JP2019/046933, filed on Dec. 2, 2019, which claims priority to Japanese Application No. 2018-227286, filed on Dec. 4, 2018. The contents of these applications are hereby incorporated by reference in their entireties.

BACKGROUND

The present invention relates to, for example, a catheter assembly and a catheter indwelling body used in a case of performing an infusion, a blood transfusion, or the like.

In a case of constructing an introduction portion of an infusion or a blood transfusion for a patient, for example, a catheter assembly as disclosed in JP 2018-511439 A is used. This catheter assembly has a catheter (flexible catheter tube), a catheter hub fixed to the catheter, and an inner needle (hollow introducer needle) arranged within the catheter. When the catheter assembly is used, the inner needle is detached from the catheter and the catheter hub after the catheter and the inner needle have been inserted into a patient's body by a user, and a medical device is inserted into the catheter hub after the detachment, thereby functioning as the introduction portion.

Further, the catheter assembly disclosed in JP 2018-511439 A includes a valve (elastic septum) that can be opened and closed and an opening member (valve actuator) arranged on a proximal side of the valve in the catheter hub. The valve prevents a leakage of blood by blocking a space inside the catheter hub at the time of detaching the inner needle. The opening member penetrates through (opens) the valve along with the insertion of the medical device, thereby enabling a medicinal liquid and blood to flow from the medical device side to the catheter.

SUMMARY OF INVENTION

Meanwhile, in the configuration in which the opening member penetrates through the valve along with the insertion of the medical device as described above, a space is formed between a distal end of the opening member through which fluid (a medicinal liquid or blood) flows out and the valve, which makes it difficult for the fluid to flow. If such a space exists, the medicinal liquid, blood, or the like is likely to remain, and a risk of growth of bacteria or the like increases.

The present invention has been made to solve the above-described problems, and an object thereof is to provide a catheter assembly and a catheter indwelling body capable of further enhancing hygiene during use by reducing the retention of the fluid with a simple configuration.

In order to achieve the above object, a catheter assembly according to a first aspect of the present invention includes: an inner needle having a blade surface at a distal end; a catheter through which the inner needle is inserted; a catheter hub through which the inner needle is inserted and that is fixed to a proximal end of the catheter; a valve that has a pair of inclined portions that are inclined so as to become closer to each other in a distal direction, an end surface located at distal ends of the pair of inclined portions, and a slit formed along a longitudinal direction of the end surface, and is located in an internal space of the catheter hub; and an opening member that is located in the internal space, is formed in a tubular shape having a space inside, is located proximal of the valve in an initial state, and moves in a distal direction to open the valve. The opening member has a side hole that causes the space to communicate with an outside of the opening member, and the side hole is located distal of a most proximal end of the slit in a state in which the valve is opened.

Further, in order to achieve the above object, a catheter indwelling body according to a second aspect of the present invention includes: a catheter; a catheter hub that has an internal space and is fixed to a proximal end of the catheter; a valve that has a pair of inclined portions that are inclined so as to become closer to each other in a distal direction, an end surface located at distal ends of the pair of inclined portions, a front slit formed along a longitudinal direction of the end surface, and a side slit formed on a side surface between the pair of inclined portions from both ends of the end surface; and an opening member that is located in the internal space, is formed in a tubular shape having a space inside, is located on a proximal side of the valve in an initial state, and moves in the a direction to open the valve by opening the front slit and the side slit. The opening member has a side hole that causes the space to communicate with an outside of the opening member, and the side hole is located at a position overlapping the open side slit in a state in which the valve is opened.

Further, in order to achieve the above object, a catheter indwelling body according to a third aspect of the present invention includes: a catheter; a catheter hub fixed to a proximal end of the catheter; a valve that has a slit and is located in an internal space of the catheter hub; and an opening member that is located in the internal space, is formed in a tubular shape having a space inside, and is located on a proximal side of the valve in an initial state, and moves in a distal direction to open the valve. The opening member includes an insertion portion that is insertable into the slit and has an outer peripheral surface and an inner peripheral surface, and at least one of the outer peripheral surface and the inner peripheral surface is formed in a tapered shape having a diameter that becomes smaller in the distal direction. The opening member includes a side hole that is located at a position opposing a site where the slit is open in a state in which the valve is opened, and causes the space to communicate with an outside of the opening member.

The catheter assembly and the catheter indwelling body have the side hole, and thus, can allow the fluid flowing in the space to flow out to a radially outer space of the opening member or the valve. That is, the side hole allows the fluid to wrap around the valve that is inclined in the distal direction through the opening. Therefore, the fluid is suppressed from remaining in an internal space on the distal side of the valve, the growth of bacteria that is likely to be caused by the retention of the fluid is reduced, and the hygiene during use can be further improved.

BRIEF DESCRIPTION OF DRAWINGS

FIG. 9A is a partial side cross-sectional view illustrating an opening member and a catheter hub according to a ninth modification. FIG. 9B is a partial side cross-sectional view illustrating a state in which a medical device is connected to the catheter hub of FIG. 9A.

FIG. 12A is a partial side cross-sectional view illustrating the opening member and a catheter hub of FIG. 11.

FIG. 12B is a partial side cross-sectional view illustrating a state in which a medical device is connected to the catheter hub of FIG. 12A.

FIG. 13A is a plan view illustrating a catheter assembly according to a first application example. FIG. 13B is a side view illustrating a catheter assembly according to a second application example.

DESCRIPTION OF EMBODIMENTS

Hereinafter, a preferred embodiment of the present invention will be described in detail with reference to the accompanying drawings.

Figure 1:
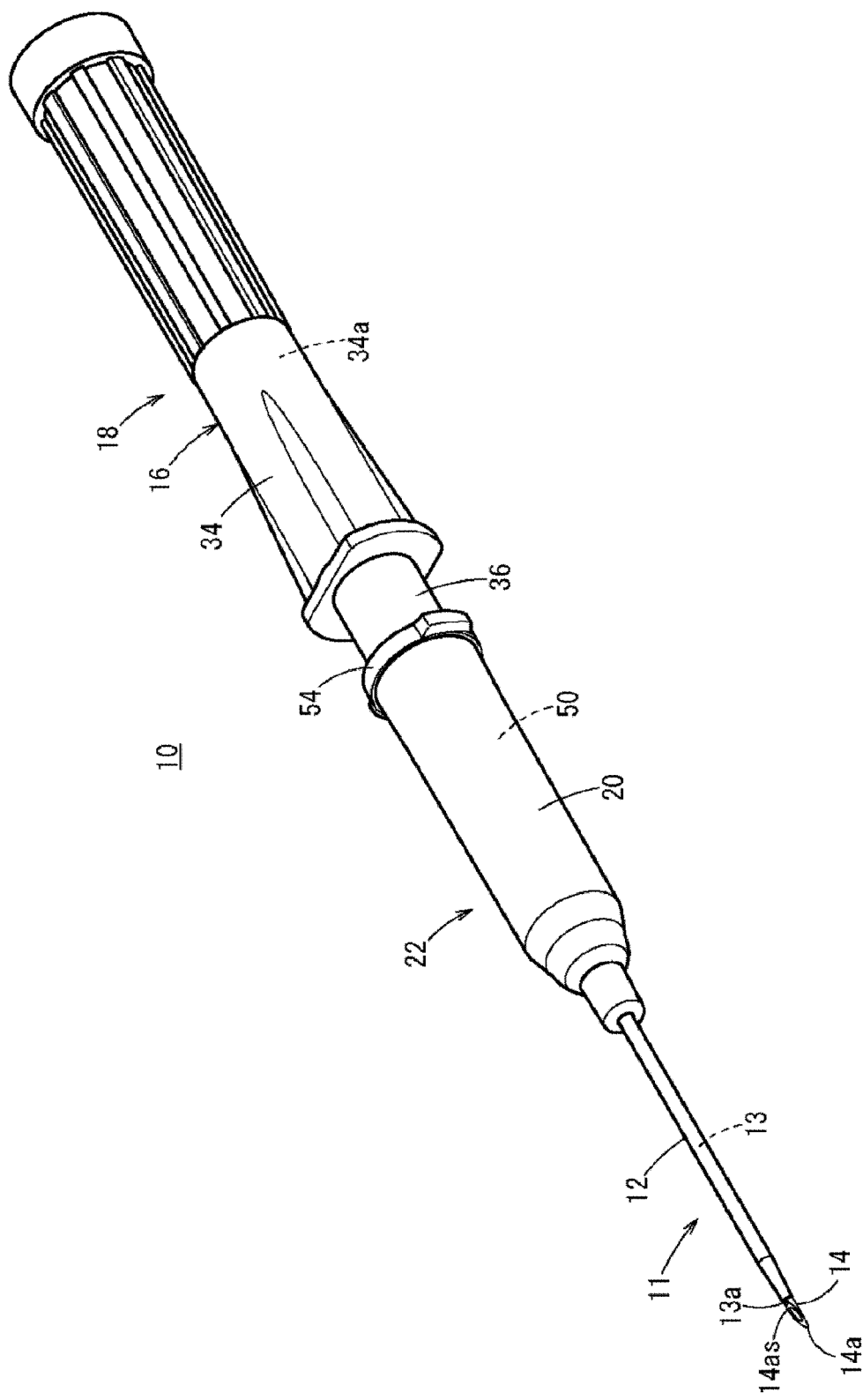
FIG. 1 is a perspective view of a catheter assembly according to one embodiment of the present invention.

A catheter assembly 10 according to a first embodiment of the present invention has a catheter 12 that is inserted to indwell inside a patient's body (living body) as illustrated in FIG. 1, and is used to construct an inlet/outlet for a liquid (a medicinal liquid and blood) during an infusion, a blood transfusion, or the like. The catheter 12 is configured as a peripheral venous catheter. Incidentally, the catheter 12 may be a catheter longer than the peripheral venous catheter (for example, a central venous catheter, a PICC, a mid-line catheter, and the like). In addition, the catheter 12 is not limited to a venous catheter, and may be configured as an arterial catheter such as a peripheral arterial catheter.

As illustrated in FIG. 1, the catheter assembly 10 has an operating body 18 formed of an inner needle 14 and a needle hub 16 fixed to a proximal end of the inner needle 14. Further, the catheter assembly 10 has a catheter indwelling body 22 formed of the above-described catheter 12 and a catheter hub 20 fixed to a proximal end of the catheter 12.

The catheter assembly 10 is assembled with the operating body 18 from the proximal side of the catheter indwelling body 22 in an initial state (product provided state) before use, thereby forming a multi-structure needle 11 through which the inner needle 14 is inserted in the catheter 12. In the multi-structure needle 11, the needle tip 14a of the inner needle 14 protrudes, and the inner needle 14 and the catheter 12 can be integrally punctured the patient. Further, a valve 24, an opening member 26, and a fixing member 28 are housed inside the catheter hub 20 as illustrated in FIG. 2.

In the use of the catheter assembly 10 illustrated in FIG. 1, a user, such as a doctor and a nurse, grips and operates the needle hub 16 in the puncture state to puncture the multi-structure needle 11 into the patient's body, thereby setting a puncture state in which the needle tip 14a reaches a blood vessel. Further, the user inserts the catheter 12 into the blood vessel by advancing the catheter 12 relative to the inner needle 14 while maintaining the puncture state. Thereafter, the inner needle 14 is retracted with respect to the catheter 12 to remove the inner needle 14 from the catheter hub 20 so that the catheter 12 indwells in the blood vessel. The catheter 12 can perform treatment such as administering a medicinal liquid or blood and sampling blood as a medical device 100 (see FIG. 4) is connected to the catheter hub 20 in the indwelling state. Hereinafter, each configuration of the catheter assembly 10 will be described in detail.

Figure 2:
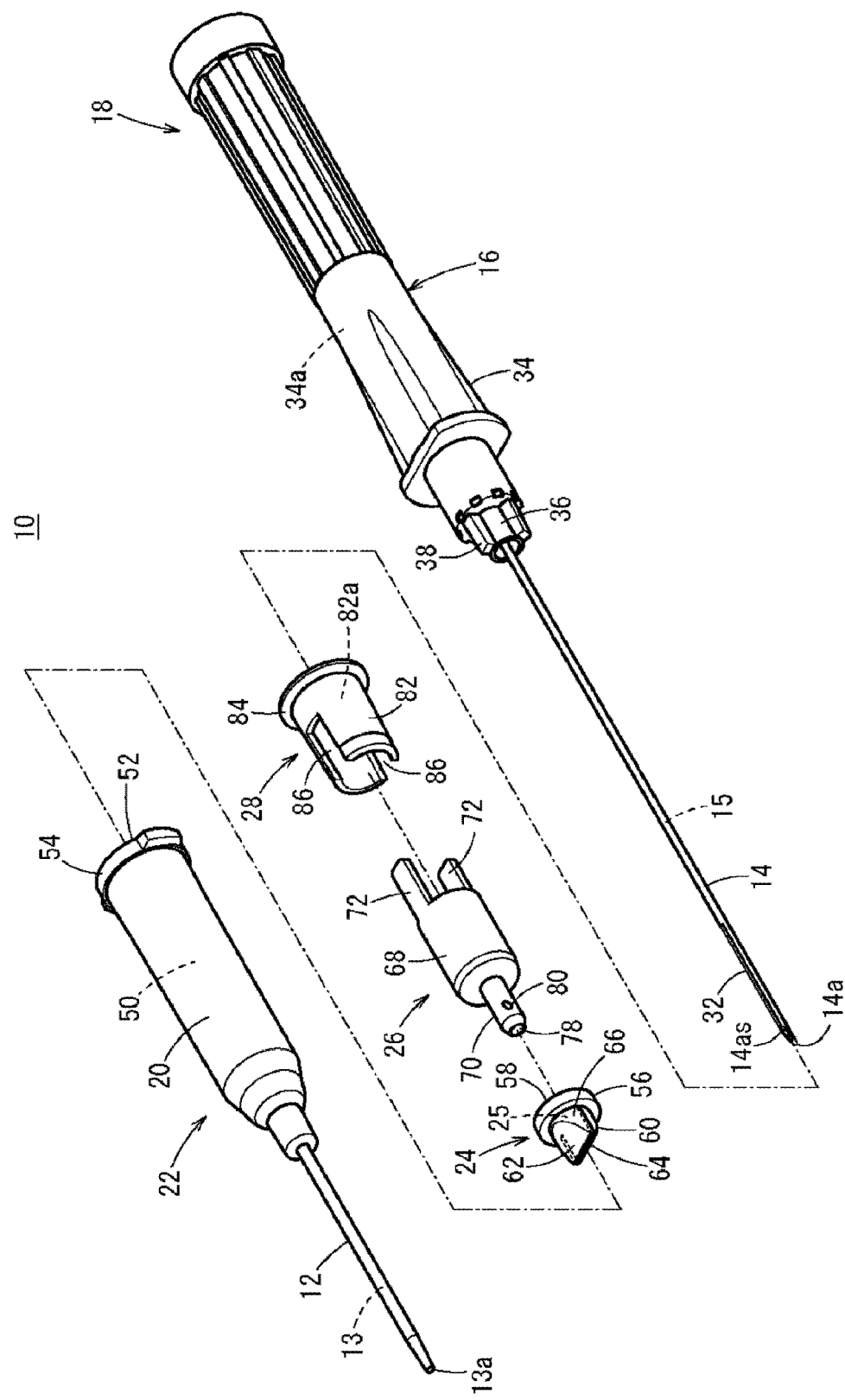
FIG. 2 is an exploded perspective view of the catheter assembly of FIG. 1.

As illustrated in FIGS. 1 and 2, the inner needle 14 of the catheter assembly 10 (the operating body 18) is configured as a hollow tube having rigidity capable of puncturing a skin of a living body, and has the sharp needle tip 14a at a distal end thereof. Inside the inner needle 14, a hollow portion 15 is provided along the axial direction. The needle tip 14a has a blade surface 14as that is inclined at a predetermined angle with respect to the axial direction of the inner needle 14 and faces the outer side of the inner needle 14 from a predetermined circumferential position of the inner needle 14. An outer peripheral surface of the inner needle 14 is provided with a groove 32 for flashback that guides blood to the proximal side when puncturing a blood vessel. Incidentally, the inner needle 14 may have a hole (not illustrated) communicating with the hollow portion 15 instead of the groove 32.

Examples of a constituent material of the inner needle 14 include a metal material such as stainless steel, aluminum or an aluminum alloy, and titanium or a titanium alloy, a hard resin, ceramics, and the like. The inner needle 14 is firmly fixed to the needle hub 16 by an appropriate fixing means such as fusion, adhesion, and insert molding.

The needle hub 16 forms a grip portion to be gripped by the user in the initial state in which the catheter indwelling body 22 and the operating body 18 are assembled. The needle hub 16 includes a tubular hub main body 34 that is directly gripped by the user, and an inner needle support portion 36 that is integrally molded at a distal end of the hub main body 34.

The hub main body 34 is formed to have a shape and a size that allow the multi-structure needle 11 to be stably operated. The hub main body 34 is formed in a cylindrical shape on the proximal side and is gradually deformed into a square tube shape toward the distal side, and has a cavity 34a having a circular cross section inside. The hub main body 34 is configured such that a cylindrical portion on the proximal side having a ridge is separable from the distal side, and a filter (not illustrated) is provided in the cavity 34a in the cylindrical portion on the proximal side.

The inner needle support portion 36 is formed in a columnar shape protruding from the hub main body 34 in the distal direction, and holds a proximal portion of the inner needle 14 at the central portion thereof. A plurality of ribs 38 are provided at equal intervals along the circumferential direction in a portion on the distal side of an outer surface of the inner needle support portion 36.

A constituent material of the needle hub 16 is not particularly limited, but a thermoplastic resin, such as polypropylene, polycarbonate, polyamide, polysulfone, polyarylate, and a methacrylate-butylene-styrene copolymer can be applied.

On the other hand, the catheter 12 of the catheter assembly 10 is configured as a flexible hollow body in which a lumen 13 is formed inside. An outer shape of the catheter 12 and the lumen 13 are formed in a perfect circular shape in cross-sectional view orthogonal to the axial direction, and extend along the axial direction of the catheter 12. The lumen 13 communicates with a distal opening 13a formed at a distal end of the catheter 12 and a proximal opening 13b (see FIG. 3) formed at a proximal end of the catheter 12.

A material forming the catheter 12 is not particularly limited, but a transparent soft resin material may be applied. Examples of a constituent material of the catheter 12 include a fluorine-based resin such as polytetrafluoroethylene (PTFE), an ethylene-tetrafluoroethylene copolymer (ETFE), and a perfluoroalkoxy fluorine resin (PFA), an olefin-based resin such as polyethylene and polypropylene or a mixture thereof, polyurethane, polyester, polyamide, a polyether nylon resin, a mixture of the olefin-based resin and an ethylene-vinyl acetate copolymer, and the like.

A length of the catheter 12 is not particularly limited, and can be appropriately designed according to the application, various conditions, and the like, and is set to, for example, about 14 to 500 mm. The proximal end of the catheter 12 is inserted and fixed inside the catheter hub 20.

The catheter hub 20 is exposed on the patient's skin in a state in which the catheter 12 has been inserted into the patient's blood vessel, and indwells together with the catheter 12 by being pasted with a tape or the like. A material forming the catheter hub 20 is not particularly limited, but, for example, the materials exemplified in the needle hub 16 may be appropriately adopted.

Figure 3:
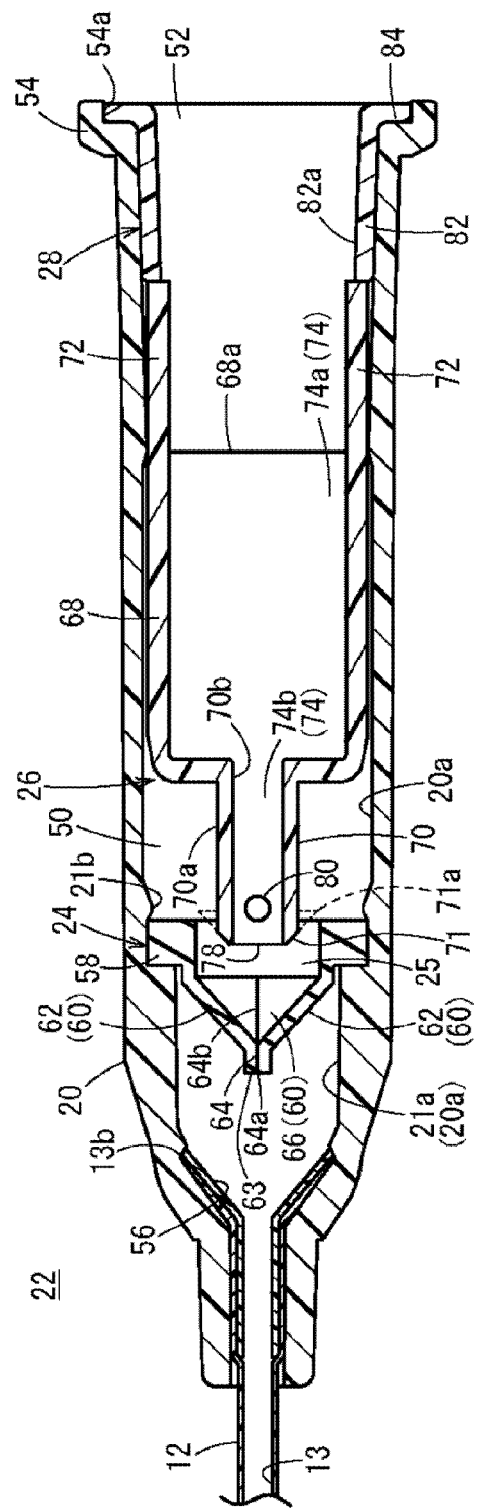
FIG. 3 is a partial side cross-sectional view illustrating a catheter hub of a catheter indwelling body.

As illustrated in FIGS. 2 and 3, the catheter hub 20 is formed in a tubular shape tapered in a distal direction. An internal space 50 is provided inside the catheter hub 20, and the internal space 50 communicates with the lumen 13 (the proximal opening 13b) of the catheter 12 on the distal side and communicates with a proximal opening portion 52 of the catheter hub 20 on the proximal side. The above-described valve 24, opening member 26, and fixing member 28 are housed in the internal space 50. Further, a flange 54 extending along the circumferential direction is provided on an outer peripheral surface of the catheter hub 20 on the proximal side.

The catheter 12 and the catheter hub 20 are fixed by an appropriate fixing means such as caulking, fusion, and adhesion. In FIG. 3, a caulking pin 56 is inserted into the internal space 50 of the catheter hub 20 to caulk the caulking pin 56 by sandwiching the catheter 12 between an inner wall 20a of the catheter hub 20 and the caulking pin 56, thereby fixing the catheter 12.

The valve 24 housed in the internal space 50 is configured as a hemostatic valve that blocks blood, which flows into the internal space 50 from the lumen 13 of the catheter 12, from leaking from the proximal opening portion 52. An example of the valve 24 is an application of a duckbill valve.

For example, the valve 24 has an annular portion 58 fixed to the inner wall 20a of the catheter hub 20 and a valve main body 60 protruding from the annular portion 58 in the distal direction. On the other hand, the inner wall 20a of the catheter hub 20 is provided with a stepped portion 21a having a smaller diameter and a locking convex portion 21b at a position away from the stepped portion 21a on the proximal side, and the valve 24 is immovably fixed by sandwiching the annular portion 58 between the stepped portion 21a and the locking convex portion 21b.

The valve main body 60 is formed in a cylindrical shape on the annular portion 58 side and is formed in a tubular shape having a pair of inclined portions 62 that are close to each other in the distal direction. A valve space 25 that narrows in the distal direction is formed inside the valve 24.

Further, an end surface 63 extending in the width direction is formed at distal ends of the pair of inclined portions 62. Further, the valve main body 60 has a slit 64. The slit 64 includes a front slit 64a formed along the longitudinal direction of the end surface 63 when viewed from the front, and a side slit 64b on an inner cylinder side portion 66 (side surface) formed between the pair of inclined portions 62 from both ends of the end surface 63. The front slit 64a and the side slit 64b are continuous, and the side slit 64b extends parallel to the axial direction of the valve 24 and extends to a distal end of the annular portion 58. The slit 64 is inserted through the inner needle 14 in an initial state and is self-closed as the inner needle 14 is removed from the valve main body 60. Further, the pair of inclined portions 62 are greatly separated from each other along with the insertion of the opening member 26 arranged on the proximal side of the valve 24 to open the slit 64 (see also FIG. 4). As a result, a force of inserting the opening member 26, which will be described later, can be reduced. Further, because the valve 24 includes the pair of inclined portions 62, the front slit 64a, and the side slit 64b, it is difficult to generate a force of returning the opening member 26 to the proximal side, and thus, the state of being inserted into the valve 24 can be easily maintained.

The opening member 26 is arranged proximal of the valve main body 60 of the internal space 50 in an initial state. The opening member 26 includes a cylindrical barrel portion 68, an insertion portion 70 that is connected to a distal end of the barrel portion 68 and protrudes in the distal direction, and a pair of extending portions 72 that are connected to a proximal end of the barrel portion 68 and protrude in the proximal direction. A space 74 of the opening member 26 is formed inside the barrel portion 68 and the insertion portion 70.

The barrel portion 68 is formed to have an outer shape slightly smaller than a diameter of the internal space 50 of the catheter hub 20, and includes a barrel-portion-side space portion 74a, which is a part of the space 74, inside. The outer shape (outer peripheral surface) of the barrel portion 68 is formed in a circular shape in cross-sectional view orthogonal to the axial direction of the opening member 26. The barrel-portion-side space portion 74a communicates with a proximal opening 68a provided at a proximal end of the barrel portion 68.

When the opening member 26 moves in the distal direction relative to the valve 24, the insertion portion 70 passes through the slit 64 of the valve 24 to push and widen the valve main body 60 (the pair of inclined portions 62). The insertion portion 70 is formed in a cylindrical shape having an outer diameter sufficiently smaller than an outer diameter of the barrel portion 68, and has a distal portion arranged on the inner side (the valve space 25) of the annular portion 58 of the valve 24 in an initial state. Further, a step between the barrel portion 68 and the insertion portion 70 (distal end surface of the barrel portion 68) is caught by the annular portion 58 of the valve 24 when the opening member 26 moves in the distal direction, thereby restricting the movement of the opening member 26 in the distal direction.

Inside the insertion portion 70, an insertion-portion-side space portion 74b, which is a part of the space 74, is formed. The insertion-portion-side space portion 74b extends along the axial direction of the insertion portion 70 and has a distal end communicating with a distal opening 78 formed at a distal end of the insertion portion 70 and a proximal end communicating with the barrel-portion-side space portion 74a. Further, a tapered surface 71 having a diameter that becomes smaller in the distal direction of the opening member 26 is formed on an outer peripheral surface of the insertion portion 70 on the distal side.

Further, the insertion portion 70 has a pair of side holes 80 proximal of a site where the tapered surface 71 is formed. The pair of side holes 80 oppose each other with the insertion-portion-side space portion 74b interposed therebetween. Each of the side holes 80 is provided at a position away from the distal opening 78 by a predetermined distance, penetrates through an outer peripheral surface 70a and an inner peripheral surface 70b of the insertion portion 70 (in the thickness direction), and causes the insertion-portion-side space portion 74b to communicate with the outside of the insertion portion 70.

The opening member 26 sets the positions of the side holes 80 such that the slit 64 formed in the inner cylinder side portion 66 of the valve 24 and the pair of side holes 80 are at the same phase (circumferential position) in an initial state. Each of the side holes 80 formed in this manner opposes a site where the slit 64 of the valve 24 (the inner cylinder side portion 66) is open when the opening member 26 opens the valve main body 60 along with the insertion of the medical device 100. That is, the pair of side holes 80 are located distal of the most proximal end of the slit 64 in a state in which the opening member 26 opens the valve 24 (see also FIG. 4).

On the other hand, the pair of extending portions 72 provided at the proximal end of the barrel portion 68 oppose each other and are formed as rectangular pieces that extend in the proximal direction by a predetermined length. Each of the extending portions 72 is formed in an arc shape following a shape of the barrel portion 68, and has a proximal end protruding inward from an inner peripheral surface of the fixing member 28. As a result, when a male connector 102 (see FIG. 4) of the medical device 100 is inserted into the catheter hub 20, the distal end of the male connector 102 comes into contact with proximal ends of the pair of extending portions 72. Therefore, the opening member 26 moves in the distal direction under a pressing force of the male connector 102.

The fixing member 28 is an inner member that prevents detachment of the opening member 26 arranged in the internal space 50 of the catheter hub 20. Further, the fixing member 28 has a function of restricting the rotation of the opening member 26 in the circumferential direction with respect to the catheter hub 20. The fixing member 28 is fixed to the catheter hub 20 by fitting the opening member 26 into the inner wall 20a of the catheter hub 20 in a state of being housed in the internal space 50. Incidentally, a fixing means between the catheter hub 20 and the fixing member 28 is not particularly limited, and may be adhesion, fusion, or the like.

The fixing member 28 includes a fixed tubular body 82 having a through-hole 82a, and an annular convex portion 84 provided at a proximal end of the fixed tubular body 82. The proximal end of the fixed tubular body 82 forms the proximal opening portion 52 of the catheter hub 20. The fixed tubular body 82 is formed with a pair of notches 86 in which the pair of extending portions 72 of the opening member 26 are arranged. The pair of notches 86 are provided at opposing positions with the through-hole 82a interposed therebetween, and extend in the proximal direction from a distal end of the fixed tubular body 82. The annular convex portion 84 is arranged in an annular groove portion 54a inside the flange 54 formed at the proximal end of the catheter hub 20 to restrict the displacement of the fixing member 28 in the distal direction.

The catheter assembly 10 according to the present embodiment is basically configured as described above, and operations thereof will be described hereinafter.

As described above, the catheter assembly 10 is used in a case of constructing the inlet/outlet for the infusion, the blood transfusion, the blood sampling, and the like with respect to the patient. The user grips and operates the needle hub 16 of the catheter assembly 10 in the initial state illustrated in FIG. 1 to puncture the patient with the multistructure needle 11.

When the needle tip 14a of the inner needle 14 reaches the blood vessel, blood flows through the groove 32 of the inner needle 14 to the lumen 13 of the catheter 12. As a result, the user can visually recognize a flashback of blood and confirm that the lumen 13 has secured the blood vessel. When flowing inside the lumen 13 of the catheter 12 in the proximal direction, the blood flows into the internal space 50 of the catheter hub 20 from the proximal opening 13b. In the internal space 50, the valve 24 is inserted through the inner needle 14, and the circumference of the inner needle 14 is sealed to prevent the blood from flowing out in the proximal direction of the valve 24.

In the puncture state, the user advances the catheter 12 relative to the inner needle 14 and inserts the catheter 12 into the blood vessel. At a stage where the catheter 12 is inserted into the blood vessel to some extent, the operating body 18 is retracted with respect to the catheter indwelling body 22. As a result, the inner needle 14 is detached from the catheter 12.

In the catheter hub 20, when the needle tip 14a of the inner needle 14 is pulled out from the valve 24, the valve main body 60 is elastically restored to close the slit 64. Accordingly, blood is prevented from moving to the proximal side of the valve 24. Further, if the inner needle 14 and the needle hub 16 are retracted, the inner needle 14 is detached from the proximal opening 13b of the catheter hub 20. That is, the operating body 18 is separated from the catheter indwelling body 22, and the user causes the catheter indwelling body 22 in which the inside of the catheter hub 20 is in the state illustrated in FIG. 3 to indwell in the patient.

Figure 4:
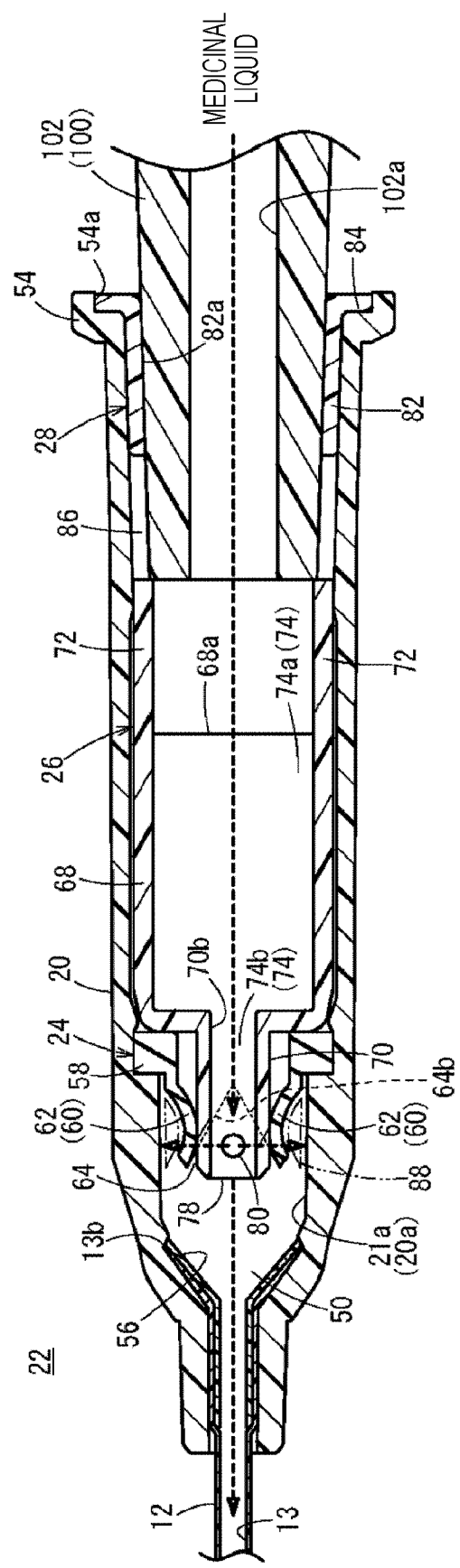
FIG. 4 is a partial side cross-sectional view illustrating an operation when a medical device is inserted into the catheter hub to cause a medicinal liquid to flow.

In the indwelling state of the catheter indwelling body 22, the user inserts the male connector 102 of the medical device 100 (a tube of an infusion line, a syringe, or the like) into the internal space 50 through the proximal opening 13b of the catheter hub 20 as illustrated in FIG. 4. When advancing inside the fixing member 28, the male connector 102 comes into contact with a proximal end of the opening member 26 (the pair of extending portions 72) protruding radially inward from the inner peripheral surface of the fixing member 28. As a result, the user pushes the opening member 26 in the distal direction at the time of connecting (inserting) the male connector 102. The pair of extending portions 72 are guided by the pair of notches 86 of the fixing member 28 to move at the time of pushing the opening member 26, thereby restricting the rotation of the opening member 26 in the circumferential direction.

The opening member 26 moves inside the valve 24 as the male connector 102 is pushed, and the insertion portions 70 separate the pair of inclined portions 62 from each other, thereby opening the slit 64. Then, the insertion portion 70 of the opening member 26 greatly separates the pair of inclined portions 62 in an insertion completion state in which the male connector 102 is fitted to the catheter hub 20 (the fixing member 28). The slit 64 of the valve 24 is deformed along an outer shape of the opening member 26, and the side slit 64b widens the gap in the distal direction. That is, as the pair of inclined portions 62 are deformed, the side slit 64b is deformed from the proximal end toward the distal end surface in an oblique direction with respect to the axis of the valve 24. Then, in the insertion completion state, the pair of side holes 80 provided in the insertion portion 70 are arranged at positions opposing each other at the site where the slit 64 (the side slit 64b) is open.

During administration of a medicinal liquid (fluid), the medical device 100 causes the medicinal liquid to flow from a flow path 102a of the male connector 102 into the internal space 50 of the catheter hub 20. This medicinal liquid flows in the distal direction of the internal space 50 and passes through the space 74 of the opening member 26. Then, a part of the medicinal liquid flows out from the distal opening 78 of the insertion portion 70 into the internal space 50 on the distal side of the valve 24, and further flows into the lumen 13 of the catheter 12 communicating with the distal side of the internal space 50. The medicinal liquid flowing into the lumen 13 is administered through the distal opening 13a of the catheter 12 inserted into the patient's blood vessel.

Further, the pair of side holes 80 provided in the insertion portion 70 also move a part of the medicinal liquid to the radially outer side of the insertion portion 70 when the medicinal liquid flows through the opening member 26. The medicinal liquid flowing out of the side hole 80 hits the inner wall 20a of the catheter hub 20 through the open slit 64. Then, the medicinal liquid hitting the inner wall 20a flows around the valve main body 60 (from the inner cylinder side portion 66 to the pair of inclined portions 62). Here, if the medicinal liquid is allowed to flow out only from the distal opening 78 of the insertion portion 70 around the valve main body 60 of the valve 24 (duckbill valve), there is a retention space 88 (see the alternate long and tow short dashes line in FIG. 4) where the fluid (medicinal liquid or blood) is likely to remain.

On the other hand, the medicinal liquid is allowed to flow around the valve main body 60 by allowing the medicinal liquid to flow out from the pair of side holes 80 in the catheter assembly 10 according to the present embodiment. As a result, the medicinal liquid promotes the flow of the fluid, and the retention space 88 can be favorably eliminated. That is, the medicinal liquid flowing out from the opening member 26 is supplied to the lumen 13 while flowing through the internal space 50 on the distal side of the valve 24 as a whole.

Incidentally, the present invention is not limited to the above-described embodiment, and various modifications can be made in accordance with a gist of the invention. For example, the valve 24 provided in the catheter hub 20 is not limited to the duckbill valve as described above, and may have various configurations. As another example of the valve 24, a configuration (so-called disc valve) having the slit 64 that can be opened and closed in a flat membrane can be applied instead of the above-described valve main body 60.

Further, the opening member 26 may be configured not only to have the two (pair) side holes 80 in the insertion portion 70, but also to have one or three or more side holes 80. Further, the opening member 26 may have a configuration in which an outer protruding portion 71a (umbrella portion) is provided at the distal end of the insertion portion 70 as indicated by a dotted line in FIG. 3. The outer protruding portion 71a is caught by an edge portion of the valve 24 forming the slit 64 in the state in which the insertion portion 70 has been inserted, so that the opening state of the valve 24 by the opening member 26 can be firmly maintained.

Hereinafter, other modifications will be described in detail with reference to FIGS. 5A to 8B. Incidentally, an element having the same configuration or the same function as that of the above-described embodiment will be denoted by the same reference sign, and the detailed description thereof will be omitted in the following description.

First Modification

Figure 5A:
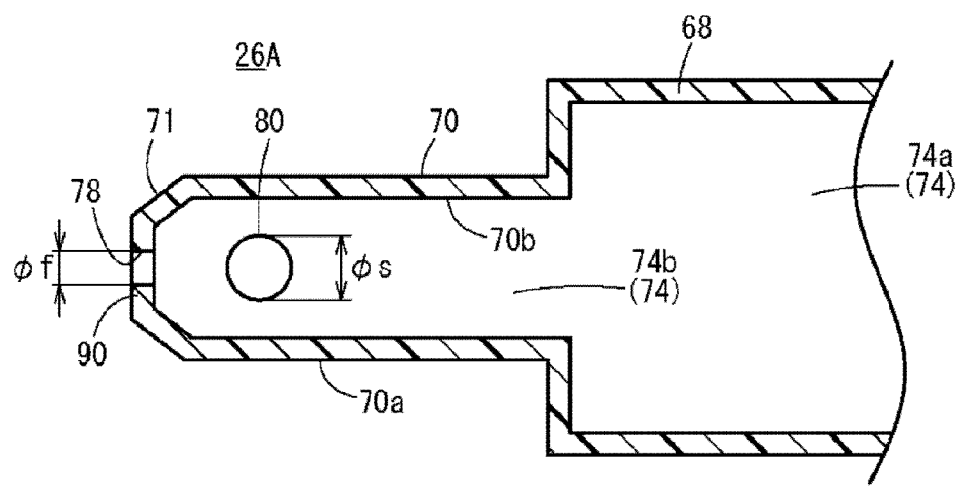
FIG. 5A is a partial side cross-sectional view schematically illustrating an opening member according to a first modification.

As illustrated in FIG. 5A, an opening member 26A according to a first modification is different from the above-described opening member 26 in that a diameter σs of the pair of side holes 80 of the insertion portion 70 is formed to be larger than a diameter σf of the distal opening 78 of the insertion portion 70. For example, the diameter σs of the pair of side holes 80 is preferably set to a size of about 1.2 to 2 times the diameter σf of the distal opening 78. Further, a distal end of the insertion portion 70 has a distal end wall 90 that protrudes to the inner side from a side wall (including the tapered surface 71) forming the insertion portion 70 to form the distal opening 78.

The opening member 26A configured in this manner suppresses the outflow amount of a medicinal liquid from the distal opening 78 and increases the outflow amount of the medicinal liquid from the pair of side holes 80 when causing the medicinal liquid to flow. Therefore, it is possible to increase the amount of the medicinal liquid that flows around the valve main body 60, and it is possible to further suppress the retention of the fluid.

Second Modification

Figure 5B:
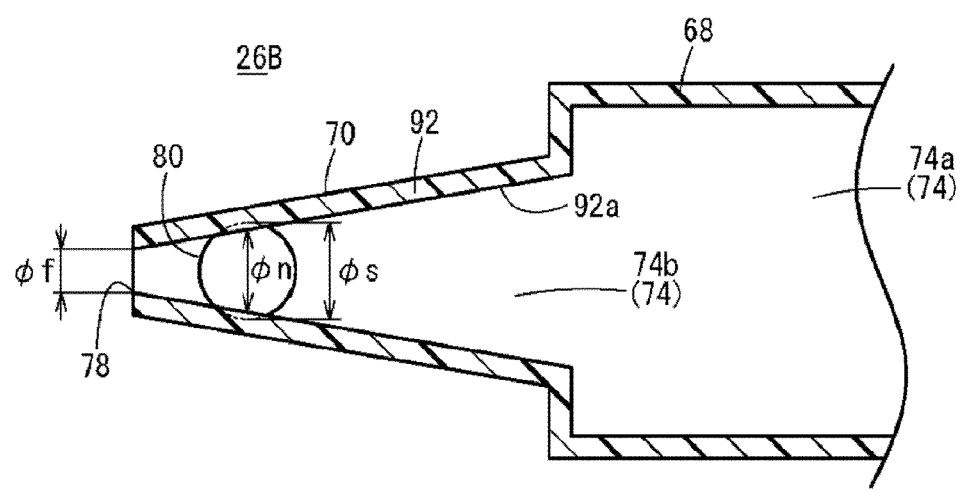
FIG. 5B is a partial side cross-sectional view schematically illustrating an opening member according to a second modification.

As illustrated in FIG. 5B, an opening member 26B according to a second modification is different from the above-described opening members 26 and 26A in that the entire insertion portion 70 is formed in a tapered conical shape (a tapered portion 92) from a distal end of the barrel portion 68 in the distal direction. Thus, an inner peripheral surface forming the insertion-portion-side space portion 74b is also formed on a tapered inner peripheral surface 92a whose diameter becomes smaller in the distal direction according to an outer shape of the insertion portion 70.

Further, the diameter σs of the pair of side holes 80 of the insertion portion 70 is formed to be larger than the diameter σf of the distal opening 78. In particular, the side hole 80 has the diameter σs larger than a diameter σn of the insertion-portion-side space portion 74b at a site where the side hole 80 is formed in the present modification. The opening member 26B configured in this manner increases the outflow amount of a medicinal liquid from the pair of side holes 80 while causing the medicinal liquid to smoothly flow in the insertion-portion-side space portion 74b. Therefore, the retention of the fluid can be further suppressed, and the medicinal liquid can be vigorously discharged from the distal opening 78.

Third Modification

Figure 6A:
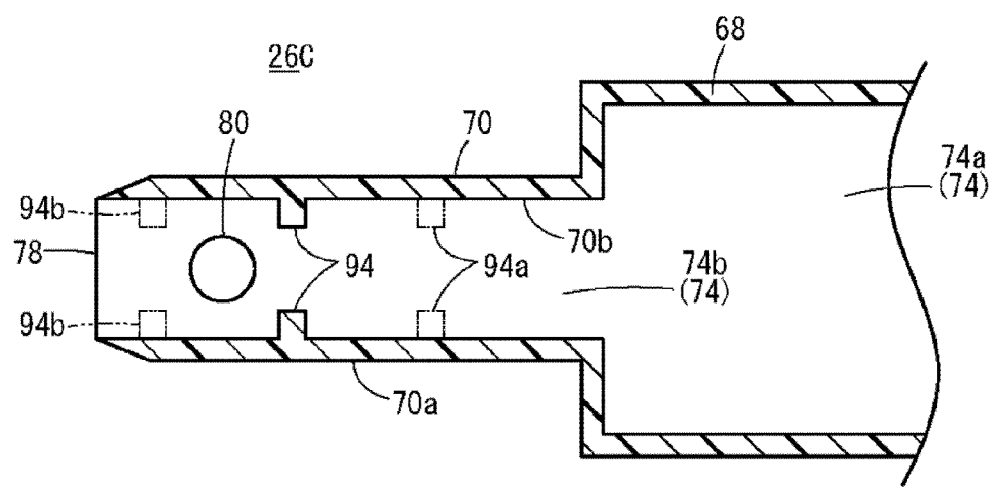
FIG. 6A is a partial side cross-sectional view schematically illustrating an opening member according to a third modification.

As illustrated in FIG. 6A, an opening member 26C according to a third modification is different from the above-described opening members 26, 26A, and 26B in that a protrusion 94 is provided on the inner peripheral surface 70b of the insertion portion 70. The protrusion 94 is provided proximal of (on an upstream side in a flow direction of a medicinal liquid) the pair of side holes 80, and slightly protrudes radially inward of the insertion-portion-side space portion 74b. Further, the protrusion 94 extends shortly along the circumferential direction of the inner peripheral surface 70b, and a plurality of the protrusions 94 are provided along the circumferential direction. Incidentally, the protrusions 94 may be formed in a ring shape that makes a circle on the inner peripheral surface 70b in a series in the circumferential direction.

The opening member 26C configured in this manner increases a turbulent flow of the medicinal liquid as the medicinal liquid flowing in the insertion-portion-side space portion 74b hits the protrusion 94. Most of the medicinal liquid in which the turbulent flow has increased is guided to the pair of side holes 80 formed on the downstream side of the protrusion 94. Accordingly, the outflow amount of the medicinal liquid from the pair of side holes 80 increases, and the retention of the fluid can be further suppressed.

Incidentally, the protrusion 94 is not limited to being formed at a position near the upstream side of the side hole 80. For example, as indicated by the alternate long and two short dashes line in FIG. 6A, the opening member 26C may be provided with a protrusion 94a at a position away from the side hole 80 in the proximal direction. This is because the outflow amount of the medicinal liquid to the side hole 80 increases if the turbulent flow of the medicinal liquid is generated by the protrusion 94a. Further, for example, the opening member 26C may have a configuration in which a protrusion 94b is provided on the distal side (downstream side in the flow direction of the medicinal liquid) of the side hole 80. The protrusion 94b formed in this manner can easily guide the medicinal liquid to the side hole 80 by allowing the medicinal liquid to flow inward.

Fourth Modification

Figure 6B:
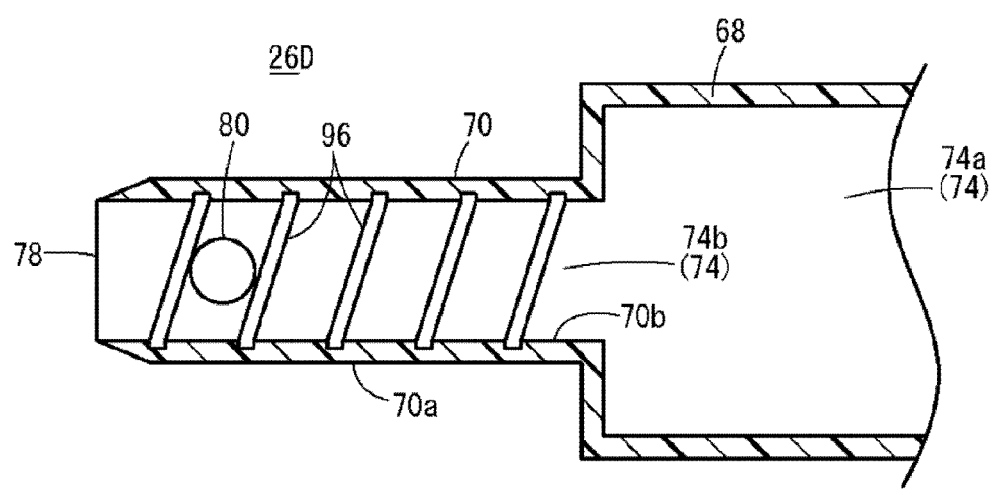
FIG. 6B is a partial side cross-sectional view schematically illustrating an opening member according to a fourth modification.

As illustrated in FIG. 6B, an opening member 26D according to a fourth modification is different from the above-described opening members 26 and 26A to 26C in that a spiral groove portion 96 is formed on the inner peripheral surface 70b of the insertion portion 70. The groove portion 96 serves to cause a medicinal liquid to flow in a spiral shape and facilitates the flow of the medicinal liquid toward the pair of side holes 80. Therefore, even in the opening member 26D, the outflow amount of the medicinal liquid from the pair of side holes 80 increases, and the retention of the fluid can be further suppressed, which is similar to the above-described opening members 26 and 26A to 26C.

Fifth Modification

Figure 7A:
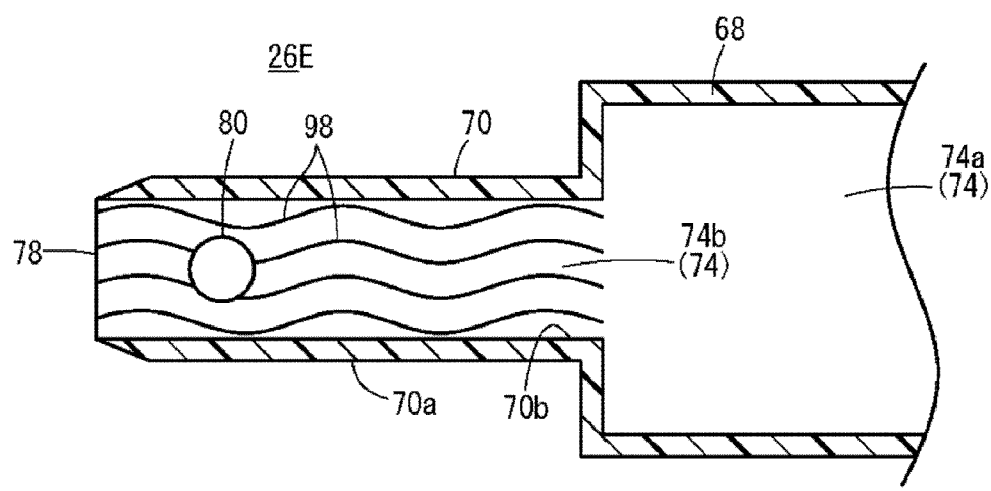
FIG. 7A is a partial side cross-sectional view schematically illustrating an opening member according to a fifth modification.

As illustrated in FIG. 7A, an opening member 26E according to a fifth modification is different from the above-described opening members 26 and 26A to 26D in that a wavy groove portion 98 is formed on the inner peripheral surface 70b of the insertion portion 70. Even in the wavy groove portion 98, a turbulent flow can be generated in a medicinal liquid flowing in the insertion-portion-side space portion 74b, and thus, the same effects as those of the opening members 26 and 26A to 26D can be obtained.

Sixth Modification

Figure 7B:
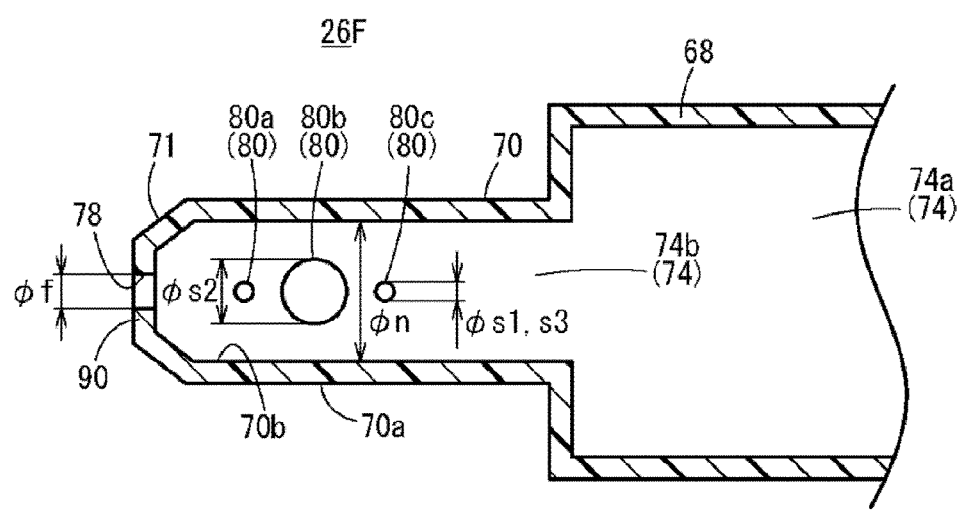
FIG. 7B is a partial side cross-sectional view schematically illustrating an opening member according to a sixth modification.

As illustrated in FIG. 7B, an opening member 26F according to a sixth modification is different from the above-described opening members 26 and 26A to 26E in terms of including a plurality of side holes 80 (three including a first side hole 80a, a second side hole 80b, and a third side hole 80c in FIG. 7B) in the axial direction of the insertion portion 70. Each pair of the first to third side holes 80a to 80c is provided in the circumferential direction of the insertion portion 70. Further, a distal end of the insertion portion 70 is provided with the distal end wall 90 such that the diameter σf of the distal opening 78 is set to be smaller than the diameter σn of the insertion-portion-side space portion 74b.

For example, a diameter σs2 of the second side hole 80b located in the middle of the three side holes 80 arrayed in the axial direction is formed to be larger than the diameter σf of of the distal opening 78 of the insertion portion 70. Diameters σs1 and σs3 of the first and third side holes 80a and 80c are formed to be smaller than the diameter σs2 of the second side hole 80b. In this manner, the sizes of the side holes 80 arrayed in the axial direction are different, and thus, it is possible to appropriately change the outflow amount of a medicinal liquid flowing out to the radially outer side of the insertion portion 70. That is, the first to third side holes 80a to 80c can distribute the medicinal liquid to the retention space 88 in an appropriate amount to flow.

Incidentally, the sizes and arrangement of the plurality of side holes 80 provided along the axial direction of the insertion portion 70 are not particularly limited. For example, the first side hole 80a may be formed to be larger than the second side hole 80b and the third side hole 80c. Further, for example, a configuration in which only the first side hole 80a and the second side hole 80b in FIG. 7B are provided may be adopted, or a configuration in which only the second side hole 80b and the third side hole 80c in FIG. 7B are provided may be adopted. The number of the side holes 80 may be one or larger than the number described in the present modification.

Seventh Modification

Figure 8A:
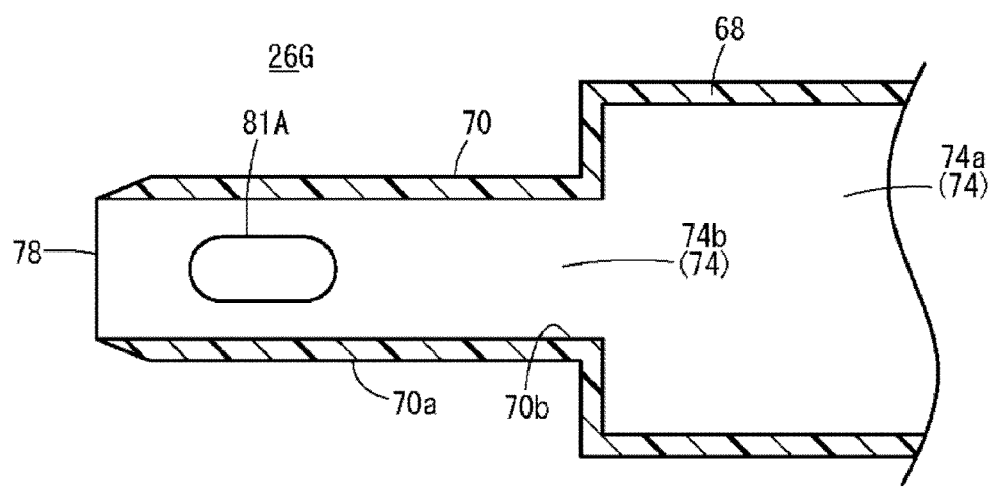
FIG. 8A is a partial side cross-sectional view schematically illustrating an opening member according to a seventh modification.

As illustrated in FIG. 8A, an opening member 26G according to a seventh modification is formed in an elliptical shape (oval shape) in which a side hole 81A has a major axis along the axial direction of the insertion portion 70. Even if the side hole 81A is formed in this manner, the outflow amount of a medicinal liquid can be increased.

Eighth Modification

Figure 8B:
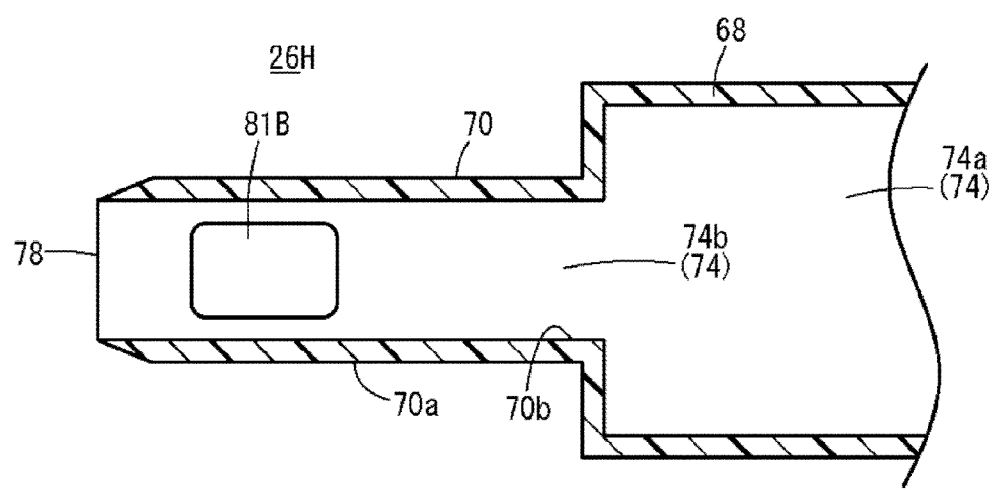
FIG. 8B is a partial side cross-sectional view schematically illustrating an opening member according to an eighth modification.

As illustrated in FIG. 8B, in an opening member 26H according to an eighth modification, a shape of a side hole 81B is formed in a rectangular shape that is long along the axial direction of the insertion portion 70. Further, corners of the rectangular are rounded. In short, shapes of the side holes 80, 81A, and 81B are not particularly limited, and various shapes capable of allowing a medicinal liquid to flow may be adopted.

Ninth Modification

Figure 10:
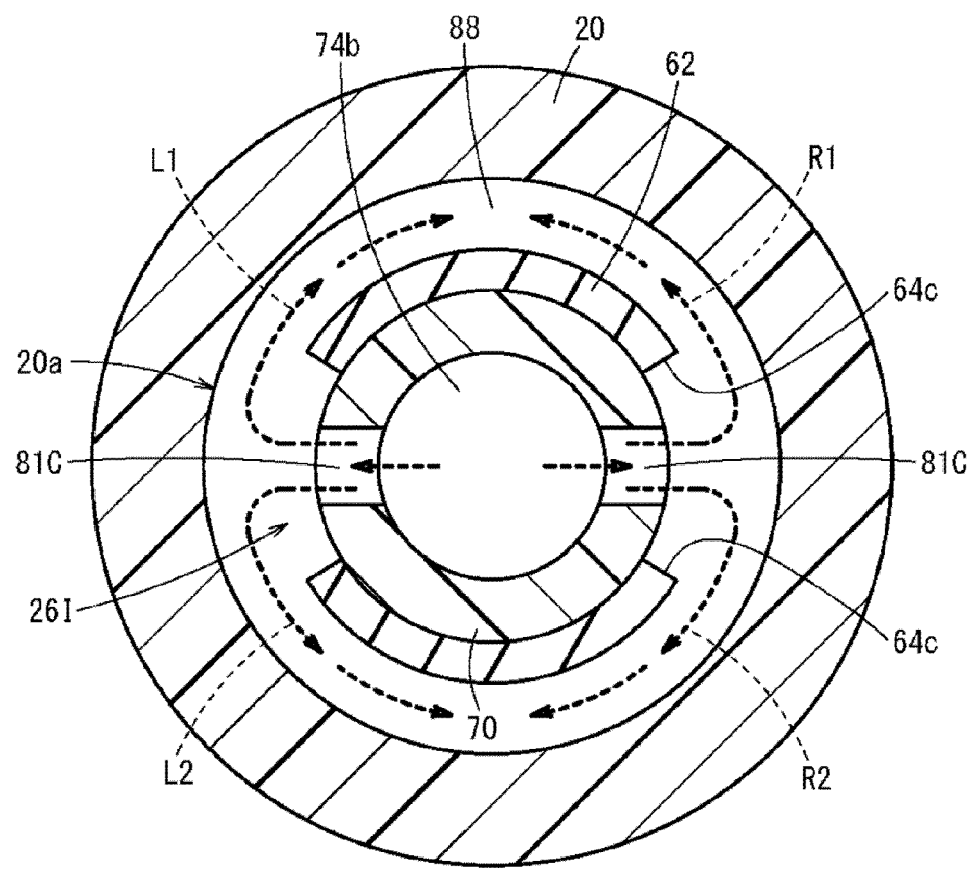
FIG. 10 is a cross-sectional view taken along line X-X of FIG. 9B.

As illustrated in FIGS. 9A, 9B, and 10, an opening member 26I according to a ninth modification has a side hole 81C having an oval shape, and the outer peripheral surface 70a and the inner peripheral surface 70b of the insertion portion 70 are formed in a tapered shape having a diameter that becomes smaller in the distal direction. The side hole 81C is provided in an axially intermediate portion of the insertion portion 70, and is formed so as to occupy a ratio of ½ or more of an axial length of the insertion portion 70. For example, a major-axis dimension of the side hole 81C (length along the axial direction of the insertion portion 70) is set to be longer than (or substantially the same as) a length along the axial direction of the side slit 64*b* of the valve 24. Further, the major-axis dimension of the side hole 81C is set to be twice or more an inner diameter of the distal opening 78. Further, a minor-axis dimension of the side hole 81C is set to a value close to a diameter of the distal opening 78 of the insertion portion 70. An area of the side hole 81C is larger than an area of the distal opening 78. As a result, fluid easily flows into the side hole 81C. The insertion portion 70 has a proximal-side portion that is sharply tapered with respect to the barrel portion 68, and a distal-side portion that is smoothly connected to the proximal-side portion and is gently tapered from the proximal-side portion. An axial length of the distal-side portion of the insertion portion 70 is formed to be longer than an axial length of the valve 24.

The opening member 26I can shift between an initial state as illustrated in FIG. 9A and an insertion completion state as illustrated in FIG. 9B. When the male connector 102 of the medical device 100 is inserted into the catheter indwelling body 22 in the initial state, the insertion portion 70 of the opening member 26I pushes and widens the slit 64. Then, when the proximal-side portion of the insertion portion 70 and the annular portion 58 of the valve 24 come into contact with each other, the insertion completion state is achieved. In this state, the insertion portion 70 arranges the distal opening 78 close to the distal side to some extent from a distal end of the valve 24. The side slit 64*b* of the valve 24 is curved so as to be far toward the distal end with respect to the axis of the valve 24.

In the insertion completion state, the opening member 26I opposes the side hole 81C over the substantially overall length (length along the axial direction) of the side slit 64*b* of the valve 24. The most proximal end of the side hole 81C overlaps a vicinity of a proximal portion of the widened side slit 64*b*. In side cross-sectional view of the insertion completion state, there are overlapping portions A1 and A2 between the side hole 81C and the valve 24 in the inner cylinder side portion 66, and a non-overlapping portion B between the side hole 81C and the valve 24 in the inner cylinder side portion 66. The sum of areas of the overlapping portions A1 and A2 is smaller than an area of the non-overlapping portion B. As a result, a large amount of a medicinal liquid flowing through the insertion-portion-side space portion 74*b* of the opening member 26I flows out from the side hole 81C through the side slit 64*b* into the internal space 50 on the distal side of the valve 24. Further, the inner peripheral surface 70*b* of the insertion portion 70 causes an appropriate turbulent flow at the proximal-side portion while smoothly guiding the medicinal liquid from the barrel portion 68 in the distal direction. As a result, the outflow amount of the medicinal liquid from the side hole 81C of the distal-side portion is increased.

The flow of the medicinal liquid flowing out from the side hole 81C will be described as follows with reference to FIG. 10, which is a cross-sectional view taken along line X-X of FIG. 9B. The medicinal liquid introduced from the medical device 100 flows into the internal space 50 on the distal side of the valve 24 from the pair of side holes 81C and the distal opening 78 (see FIG. 9B) through the insertion-portion-side space portion 74*b*. At that time, the medicinal liquid advances to the inner wall 20*a* of the catheter hub 20 from a portion between opposing surfaces 64*c* of the side slit 64*b* in the open state. Here, the flow of the medicinal liquid is divided into upper flows R1 and L1 in the drawing and lower flows R2 and L2. Each flow advances along a space between the inner wall 20*a* and an outer surface of the inclined portion 62 of the valve main body 60. Further, the flows R1 and L1 and the flows R2 and L2 reach the retention space 88 and merge with each other to push and cause a liquid in the retention space 88, which tends to remain, to flow to the distal side (front side in the drawing). Because the medicinal liquid flows around the valve main body 60 in this manner, the medicinal liquid promotes the flow of the fluid, and the retention space 88 can be favorably eliminated.

Tenth Modification

Figure 11:
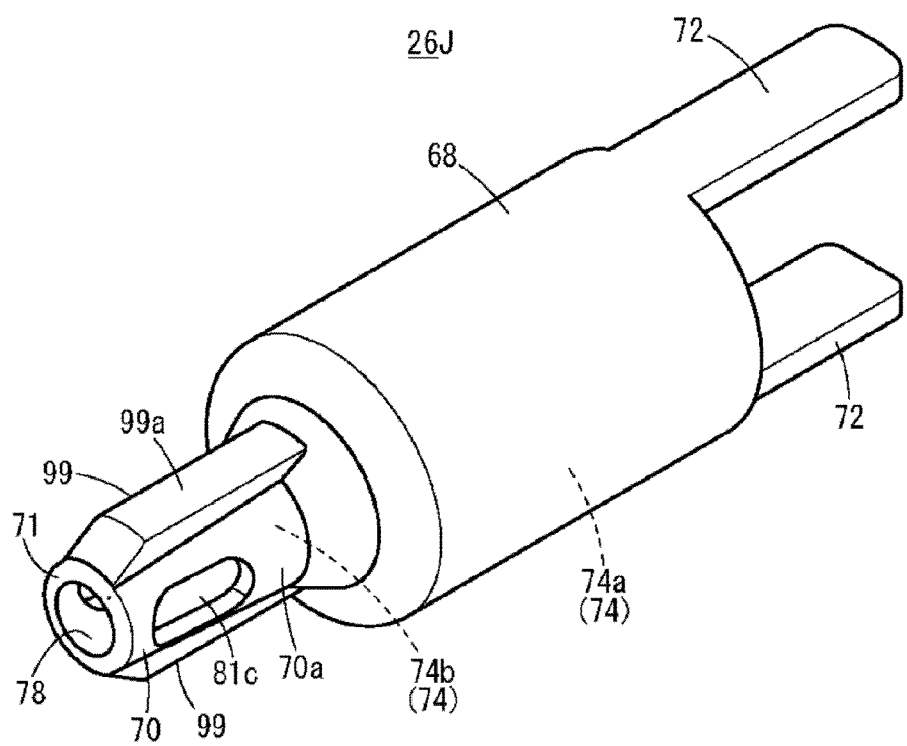
FIG. 11 is a perspective view illustrating an opening member according to a tenth modification.

As illustrated in FIG. 11, an opening member 26J according to a tenth modification has one or more ribs 99 (a pair in the present modification) on the outer peripheral surface 70*a* of the insertion portion 70. Incidentally, a shape of the opening member 26J other than the rib 99 (including the side hole 81C) is the same as that of the opening member 26I of the ninth modification, and thus, a specific description thereof will be omitted.

The pair of ribs 99 are formed at positions shifted by a phase of 90° with respect to the pair of side holes 81C in the circumferential direction of the insertion portion 70. As illustrated in FIGS. 11 and 12A, the pair of ribs 99 are provided on a distal-side portion of the insertion portion 70 having a gentle inclination, and proximal ends thereof are connected to a proximal-side portion of the insertion portion 70. Protruding portions 99*a* of the pair of ribs 99 extending at positions separated from the outer peripheral surface 70*a* extend parallel to the axial direction of the opening member 26J (the insertion portion 70).

As illustrated in FIG. 12B, the opening member 26J having the ribs 99 described above expands the pair of inclined portions 62 in the valve main body 60 as much as possible in the radial direction as the respective ribs 99 come into contact with inner surfaces of the pair of inclined portions 62 when the insertion portion 70 moves in the valve main body 60 in the distal direction. As a result, when transitioning to the insertion completion state, the side slit 64*b* opposing the pair of side holes 81C is opened more widely, which has an effect of pushing out remaining blood or medicinal liquid.

First Application Example

Further, as in a first application example illustrated in FIG. 13A, the catheter assembly 10 has a configuration in which the side slit 64*b* of the valve 24 opposes a circumferential position of the inner needle 14 corresponding to a direction in which the blade surface 14*as* faces in an assembled state. That is, the side slit 64*b* of the valve 24 and the side hole 80 or 81A to 81C of the opening member 26 or 26A to 26J are assembled so as to have the same phase as the blade surface 14*as* of the inner needle 14.

Here, at the time of assembling the catheter assembly 10, the inner needle 14 held by the needle hub 16 is inserted from the proximal side of the catheter hub 20, and the catheter 12 is caused to pass through the opening members 26 and 26A to 26J and the valve 24. In particular, the catheter assembly 10 maintains the above-described phase even if the straightness of the inner needle 14 is reduced, and thus, the needle tip 14*a* (the blade surface 14*as*) can smoothly pass through the front slit 64*a* of the valve 24 by being prevented from piercing the valve 24. The inner needle 14 is likely to bend (decrease in straightness) toward the circumferential position (or a position opposite to the circumferential position) corresponding to a direction in which the blade surface 14*as* faces at the time of forming the groove 32 or a flashback notch. The catheter assembly 10 can easily allow the insertion of the inner needle 14 because the blade surface 14*as* opposes the side slit 64*b*, and the inner needle 14 whose straightness has decreased bends in a direction along the front slit 64*a* (a direction toward the back of the paper surface or a direction toward the front of the paper surface in FIG. 13A). Therefore, the catheter assembly 10 can be assembled favorably according to an arrangement relationship in FIG. 13A.

Second Application Example

Further, as in a second application example illustrated in FIG. 13B, the catheter assembly 10 may have a configuration in which one of the pair of inclined portions 62 of the valve 24 opposes a circumferential position of the inner needle 14 corresponding to a direction in which the blade surface 14*as* faces in an assembled state. That is, the side slit 64*b* of the valve 24 and the side hole 80 or 81A to 81C of the opening member 26 or 26A to 26J are assembled so as to be orthogonal to the blade surface 14*as* of the inner needle 14.

In the catheter assembly 10 configured in this manner, the width direction of the needle tip 14*a* (blade surface 14*as*) and the front slit 64*a* of the valve 24 are parallel to each other. Thus, at the time of assembling the catheter assembly 10, it is possible to prevent the blade surface 14*as* from advancing along the inclined portion 62 and piercing the valve 24. Therefore, the catheter assembly 10 can be favorably assembled even in an arrangement relationship illustrated in FIG. 13B.

Incidentally, it is a matter of course that the above-described configurations of the opening members 26 and 26A to 26J can be applied to the other opening members 26 and 26A to 26J by taking out some of the configurations. Similarly, the arrangement relationships in the first and second application examples can be applied to various examples.

Technical ideas and effects that can be grasped from the above-described embodiment are described as follows.

The catheter assembly 10 has the side hole 80 or 81A to 81C located distal of the most proximal end of the slit 64 in the state in which the valve 24 is opened, and thus, can cause the fluid flowing through the space 74 to flow out to the space on the radially outer side of the opening members 26 and 26A to 26J and the valve 24. That is, the side hole 80 allows the fluid to wrap around the valve 24 that is inclined in the distal direction through the opening. Therefore, the fluid is suppressed from remaining in the internal space 50 on the distal side of the valve 24, the growth of bacteria that is likely to be caused by the retention of the fluid is reduced, and the hygiene during use can be further improved.

Further, the slit 64 continuously extends to the side surface (the inner cylinder side portion 66) between the pair of inclined portions 62. The catheter assembly 10 can cause the fluid to favorably flow around the valve 24 through the side holes 80 and 81A to 81C because the slit 64 extends along the inner cylinder side portion 66.

Further, the side hole 80 opposes the open slit 64 on the side surface in the state in which the valve 24 is opened. As a result, the opening members 26 and 26A to 26J can cause the fluid to flow out through the side hole 80 and the slit 64 on the side surface of the valve 24, and spread the fluid throughout the internal space 50 on the distal side of the valve 24. Accordingly, the retention of the fluid can be further suppressed.

Further, the valve 24 causes the slit 64 extending to the side surface to oppose the circumferential position of the inner needle 14 corresponding to a direction in which the blade surface 14*as* faces. As a result, the catheter assembly 10 can prevent the needle tip 14*a* from piercing the valve 24 during assembly and allow the needle tip 14*a* to favorably pass through the slit 64 even if the straightness of the inner needle 14 is reduced. Therefore, the assembly of the catheter assembly 10 can be performed with good yield and efficiency.

Further, the valve 24 causes one of the pair of inclined portions 62 to oppose the circumferential position of the inner needle 14 corresponding to a direction in which the blade surface 14*as* faces. Even in this case, the blade surface 14*as* is guided to one of the inclined portions 62 at the time of assembly, so that the catheter assembly 10 can prevent the needle tip 14*a* from piercing the valve 24 and allow the needle tip 14*a* to favorably pass through the slit 64.

Further, the opening members 26 and 26A to 26J are provided with the insertion portion 70 that can be inserted into the slit 64 and has the outer peripheral surface 70*a* and the inner peripheral surface 70*b*, and at least one of the outer peripheral surface 70*a* and the inner peripheral surface 70*b* is formed in the tapered shape having the diameter that becomes smaller in the distal direction. As a result, the catheter assembly 10 can cause the medicinal liquid to favorably flow out from the side holes 80 and 81A to 81C toward the axial center portion in the insertion portion 70.

Further, the rib 99 protruding in the opening direction of the valve 24 is provided on the outer peripheral surface 70*a* of the insertion portion 70. As a result, when the insertion portion 70 passes through the slit 64 (the side slit 64*b*) of the valve 24, the pair of inclined portions 62 can be further separated from each other, and the slit 64 is greatly opened. Therefore, the opening member 26J can cause the medicinal liquid to favorably flow out to the side through the slit 64.

Further, the opening members 26A, 26B, and 26F preferably have the distal opening 78 communicating with the space 74, and the diameter σs of the side hole 80 is preferably larger than the diameter σf of the distal opening 78. The opening members 26A, 26B, and 26F can discharge more fluid from the side hole 80 because the diameter σs of the side hole 80 is larger than the diameter σf of the distal opening 78. As a result, the retention of the fluid can be further suppressed.

Further, the inner peripheral surface (the tapered inner peripheral surface 92*a*) forming the space 74 may be formed in a tapered shape having a diameter that becomes smaller in the distal direction, and the side hole 80 may be provided at a position where the diameter σs of the side hole 80 is larger than the diameter σn of the tapered inner peripheral surface 92*a*. The opening member 26B can discharge more fluid from the side hole 80 because the diameter σs of the side hole 80 is larger than the diameter σn of the tapered inner peripheral surface 92*a*.

Further, the opening members 26C to 26E may have the protrusion 94 protruding radially inward and/or the groove portions 96 and 98 guiding the fluid in the direction different from the axial direction of the space 74, on the inner peripheral surface 70*b* forming the space 74. The opening members 26C to 26E can generate the turbulent flow in the fluid flowing through the space 74 by the protrusion 94 and the groove portions 96 and 98, and this turbulent flow makes it possible to guide a large amount of fluid to the side hole 80.

Further, the opening member 26F may have the plurality of side holes 80 (first to third side holes 80*a* to 80*c*) along the axial direction of the space 74. As a result, the opening member 26F can appropriately distribute the fluid to the plurality of side holes 80 to flow out to the radially outer side of the valve 24, so that the fluid can flow around the outer side of the valve 24.

Further, the catheter indwelling body 22 includes: the catheter 12; the catheter hub 20 that has the internal space 50 and is fixed to the proximal end of the catheter 12; the valve 24 that has the pair of inclined portions 62 close to each other in the distal direction, the end surface 63 provided at the distal ends of the pair of inclined portions 62 and extending in the width direction, the front slit 64a formed along the longitudinal direction of the end surface 63, and the side slit 64b formed on the side surface (inner cylinder side portion 66) between the pair of inclined portions 62 from both ends of the end surface 63; and the opening member 26 or 26A to 26J that is provided in the internal space 50, is formed in the tubular shape having the space 74 inside, is located proximal of the valve 24 in the initial state, and moves in the distal direction to open the valve 24 by opening the front slit 64a and the side slit 64b. The opening member 26 or 26A to 26J has the side hole 80 or 81A to 81C that causes the space 74 to communicate with the outside of the opening member 26 or 26A to 26J, and the side hole 80 or 81A to 81C is provided at the position overlapping the open side slit 64b in the state in which the valve 24 is opened.

Further, the valve 24 has the inner cylinder side portion 66. In the side cross-sectional view of the insertion completion state, the side hole 80 or 81A to 81C and the inner cylinder side portion 66 have the overlapping portions A1 and A2 and the non-overlapping portion B, and the sum of the areas of the overlapping portions A1 and A2 is smaller than the area of the non-overlapping portion B. As a result, the catheter indwelling body 22 can allow a large amount of fluid to flow to the side of the valve 24 through the side hole 80 or 81A to 81C.

Further, the catheter indwelling body 22 includes: the catheter 12; the catheter hub 20 fixed to the proximal end of the catheter 12; the valve 24 that has the slit 64 and is provided in the internal space 50 of the catheter hub 20; and the opening member 26 or 26A to 26J that is provided in the internal space 50, is formed in the tubular shape having the space 74 inside, and is located proximal of the valve 24 in the initial state, and moves in the distal direction to open the valve 24. The opening member 26 or 26A to 26J includes the insertion portion 70 that is insertable into the slit 64 and has the outer peripheral surface 70a and the inner peripheral surface 70b, and at least one of the outer peripheral surface 70a and the inner peripheral surface 70b is formed in the tapered shape having the diameter that becomes smaller in the distal direction. The opening member 26 or 26A to 26J includes the side hole 80 or 81A to 81C that is located at the position opposing the site where the slit 64 is open in the state in which the valve 24 is opened, and causes the space 74 to communicate with the outside of the opening member 26 or 26A to 26J.

As described above, the catheter indwelling body 22 can further enhance the hygiene during use by reducing the retention of the fluid with the simple configuration.

The invention claimed is:

1. A catheter assembly comprising:
an inner needle having a blade surface at a distal end;
a catheter through which the inner needle is inserted;
a catheter hub through which the inner needle is inserted and that is fixed to a proximal end of the catheter;
a valve located in an internal space of the catheter hub, wherein the valve comprises a pair of inclined portions that are inclined so as to become closer to each other in a distal direction, an end surface located at distal ends of the pair of inclined portions, a front slit formed along a longitudinal direction of the end surface, and a pair of side slits formed on side surfaces between the pair of inclined portions from both ends of the end surface, wherein, in a side cross-sectional view of the valve, the side slits extend parallel to an axial direction of the valve from the front slit to proximal ends of the inclined portions; and
an opening member that is located in the internal space, is formed in a tubular shape, has a space inside, is located proximal of the valve in an initial state, and is configured to move in a distal direction to open the valve, wherein:
the opening member comprises a side hole that causes the space to communicate with an outside of the opening member, and
the side hole is located distal of a most proximal end of at least one of the side slits in a state in which the valve is opened.

2. The catheter assembly according to claim 1, wherein:
the side hole opposes a portion of a first of the side slits that is open on a first of the side surfaces in the state in which the valve is opened.

3. The catheter assembly according to claim 1, wherein:
the valve causes a portion of a first of the side slits located on a first of the side surfaces to oppose a circumferential position of the inner needle corresponding to a direction in which the blade surface faces.

4. The catheter assembly according to claim 1, wherein:
the valve causes one of the pair of inclined portions to oppose a circumferential position of the inner needle corresponding to a direction in which the blade surface faces.

5. The catheter assembly according to claim 1, wherein:
the opening member comprises an insertion portion that is insertable into the front slit and has an outer peripheral surface and an inner peripheral surface, and the outer peripheral surface is formed in a tapered shape having a diameter that becomes smaller in the distal direction.

6. The catheter assembly according to claim 1, wherein:
the opening member comprises an insertion portion that is insertable into the front slit and has an outer peripheral surface and an inner peripheral surface, and the inner peripheral surface is formed in a tapered shape having a diameter that becomes smaller in the distal direction.

7. The catheter assembly according to claim 5, wherein:
a rib protruding in an opening direction of the valve is located on the outer peripheral surface of the insertion portion.

8. The catheter assembly according to claim 1, wherein:
the opening member comprises a distal opening that communicates with the space, and
a diameter of the side hole is larger than a diameter of the distal opening.

9. The catheter assembly according to claim 1, wherein:
an inner peripheral surface forming the space is formed in a tapered shape having a diameter that becomes smaller in the distal direction, and
the side hole is located at a position where a diameter of the side hole is larger than a diameter of the inner peripheral surface.

10. The catheter assembly according to claim 1, wherein:
the opening member comprises, on an inner peripheral surface forming the space, a protrusion that protrudes radially inward that is configured to guide fluid in a direction different from an axial direction of the space.

11. The catheter assembly according to claim 1, wherein:
the opening member comprises, on an inner peripheral surface forming the space, a groove portion that is configured to guide fluid in a direction different from an axial direction of the space.

12. The catheter assembly according to claim 1, wherein:
the opening member comprises a plurality of the side holes along the axial direction of the space.

13. A catheter indwelling body comprising:
a catheter;
a catheter hub that defines an internal space and is fixed to a proximal end of the catheter;
a valve located in an internal space of the catheter hub, wherein the valve comprises a pair of inclined portions that are inclined so as to become closer to each other in a distal direction, an end surface located at distal ends of the pair of inclined portions, a front slit formed along a longitudinal direction of the end surface, and a pair of side slits formed on side surfaces between the pair of inclined portions from both ends of the end surface, wherein, in a side cross-sectional view of the valve, the side slits extend parallel to an axial direction of the valve from the front slit to proximal ends of the inclined portions; and
an opening member that is located in the internal space, is formed in a tubular shape having a space inside, is located proximal of the valve in an initial state, and is configured to move in a distal direction to open the valve by opening the front slit and the side slits, wherein
the opening member comprises a side hole that causes the space to communicate with an outside of the opening member, and
the side hole is located at a position overlapping at least one of the open side slits in a state in which the valve is opened.

14. The catheter indwelling body according to claim 13, wherein:
the valve comprises an inner cylinder side portion, and the side hole and the inner cylinder side portion have overlapping portions and a non-overlapping portion in side cross-sectional view of an insertion completion state, and a sum of areas of the overlapping portions is smaller than an area of the non-overlapping portion.

15. A catheter indwelling body comprising:
a catheter;
a catheter hub fixed to a proximal end of the catheter;
a valve located in an internal space of the catheter hub, wherein the valve comprises a pair of inclined portions that are inclined so as to become closer to each other in a distal direction, an end surface located at distal ends of the pair of inclined portions, a front slit formed along a longitudinal direction of the end surface, and a pair of side slits formed on side surfaces between the pair of inclined portions from both ends of the end surface, wherein, in a side cross-sectional view of the valve, the side slits extend parallel to an axial direction of the valve from the front slit to proximal ends of the inclined portions; and
an opening member that is located in the internal space, is formed in a tubular shape having a space inside, is located proximal of the valve in an initial state, and is configured to move in a distal direction to open the valve, wherein:
the opening member comprises an insertion portion that is insertable into the front slit and has an outer peripheral surface and an inner peripheral surface, and at least one of the outer peripheral surface and the inner peripheral surface is formed in a tapered shape having a diameter that becomes smaller in the distal direction, and
the opening member comprises a side hole that is located at a position opposing at least one of the open side slits in a state in which the valve is opened, and causes the space to communicate with an outside of the opening member.

16. The catheter assembly according to claim 1, wherein:
the valve comprises an annular portion fixed to an inner wall of the catheter hub, and a valve main body that protrudes from the annular portion in a distal direction and comprises the pair of inclined portions, the end surface, the front slit, and the pair of side slits, and
in a side cross-sectional view of the valve, the side slits extend parallel to the axial direction of the valve from the front slit to a distal end of the annular portion.

17. The catheter indwelling body according to claim 13, wherein:
the valve comprises an annular portion fixed to an inner wall of the catheter hub, and a valve main body that protrudes from the annular portion in a distal direction and comprises the pair of inclined portions, the end surface, the front slit, and the pair of side slits, and
in a side cross-sectional view of the valve, the side slits extend parallel to the axial direction of the valve from the front slit to a distal end of the annular portion.

18. The catheter indwelling body according to claim 15, wherein:
the valve comprises an annular portion fixed to an inner wall of the catheter hub, and a valve main body that protrudes from the annular portion in a distal direction and comprises the pair of inclined portions, the end surface, the front slit, and the pair of side slits, and
in a side cross-sectional view of the valve, the side slits extend parallel to the axial direction of the valve from the front slit to a distal end of the annular portion.

* * * * *